United States Patent
Saito et al.

(10) Patent No.: US 10,145,786 B2
(45) Date of Patent: Dec. 4, 2018

(54) BONDED STRUCTURE AND BONDING-CONDITION DETECTING METHOD

(71) Applicants: MITSUBISHI HEAVY INDUSTRIES, LTD., Tokyo (JP); THE UNIVERSITY OF TOKYO, Tokyo (JP)

(72) Inventors: Nozomi Saito, Tokyo (JP); Takayuki Shimizu, Tokyo (JP); Toshio Abe, Tokyo (JP); Nobuo Takeda, Tokyo (JP); Shu Minakuchi, Tokyo (JP); Keigo Uhira, Tokyo (JP)

(73) Assignees: MISTUBISHI HEAVY INDUSTRIES, LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 9 days.

(21) Appl. No.: 14/784,600

(22) PCT Filed: Feb. 27, 2014

(86) PCT No.: PCT/JP2014/054826
§ 371 (c)(1),
(2) Date: Oct. 15, 2015

(87) PCT Pub. No.: WO2014/185119
PCT Pub. Date: Nov. 20, 2014

(65) Prior Publication Data
US 2016/0069793 A1    Mar. 10, 2016

(30) Foreign Application Priority Data

May 14, 2013   (JP) .................................. 2013-102254

(51) Int. Cl.
*G01L 9/00*    (2006.01)
*G01N 21/23*   (2006.01)
(Continued)

(52) U.S. Cl.
CPC ............... *G01N 21/23* (2013.01); *B32B 3/08* (2013.01); *B32B 5/26* (2013.01); *B32B 7/12* (2013.01);
(Continued)

(58) Field of Classification Search
CPC ............. G01N 21/23; G01N 2201/088; G01D 5/35338; G01D 5/35351; G01L 11/025; B32B 3/08; B32B 2307/42; G01B 11/16
(Continued)

(56) References Cited

U.S. PATENT DOCUMENTS 5,015,842 A * 5/1991 Fradenburgh et al. ..................... G08B 13/126 250/227.15
5,281,388 A * 1/1994 Palmer et al. ........ B29C 70/443 264/257

(Continued)

FOREIGN PATENT DOCUMENTS

CN    1202964 A    12/1998
CN    102841052 A   12/2012
(Continued)

OTHER PUBLICATIONS

English Machine Translation and Bibliographic Data for WO2013071914A1, Date May 23, 2013, Publisher: Espacenet, European Patent Office, pages: 8 total.*
(Continued)

Primary Examiner — Lisa Caputo
Assistant Examiner — Roger Hernandez-Prewit
(74) Attorney, Agent, or Firm — Wenderoth, Lind & Ponack, L.L.P.

(57) ABSTRACT

A bonded structure includes a first member, a second member, an adhesive that bonds the first member and the second member together, and an optical fiber sandwiched between
(Continued)

the first member and the second member. When pressure is applied to the optical fiber only from a predetermined direction, the sectional shape of the optical fiber changes to an elliptical shape, so that birefringence occurs, whereby the shape of the light spectrum changes so as to have multiple peaks. The optical fiber is used as a sensor for detecting the bonding condition between the first member and the second member based on the birefringence.

10 Claims, 11 Drawing Sheets

(51) Int. Cl.
B32B 7/12 (2006.01)
G01D 5/353 (2006.01)
B32B 5/26 (2006.01)
G01L 11/02 (2006.01)
B32B 3/08 (2006.01)

(52) U.S. Cl.
CPC ..... *G01D 5/35338* (2013.01); *G01D 5/35351* (2013.01); *G01L 11/025* (2013.01); *B32B 2262/106* (2013.01); *B32B 2307/42* (2013.01); *B32B 2605/00* (2013.01); *B32B 2605/18* (2013.01); *G01N 2201/088* (2013.01)

(58) Field of Classification Search
USPC .................. 73/705, 179; 250/227.15; 156/64
See application file for complete search history.

(56) References Cited

U.S. PATENT DOCUMENTS

| | | | |
|---|---|---|---|
| 5,399,854 | A | 3/1995 | Dunphy et al. |
| 5,469,520 | A | 11/1995 | Morey et al. |
| 5,770,155 | A | 6/1998 | Dunphy et al. |
| 5,828,059 | A | 10/1998 | Udd |
| 6,254,215 | B1 | 7/2001 | Hiroki et al. |
| 8,327,716 | B2 * | 12/2012 | Kreuzer et al. ...... G01B 11/165 73/800 |
| 9,244,007 | B2 | 1/2016 | Fukuzawa et al. |
| 2003/0085938 | A1 | 5/2003 | Imanaka et al. |
| 2004/0206893 | A1 | 10/2004 | Sato |
| 2006/0081772 | A1 | 4/2006 | Williams et al. |
| 2006/0104561 | A1 | 5/2006 | Ivtsenkov |
| 2012/0327401 | A1 | 12/2012 | Fukuzawa et al. |
| 2014/0071454 | A1 | 3/2014 | Fukuzawa et al. |

FOREIGN PATENT DOCUMENTS

| | | | |
|---|---|---|---|
| EP | 0 967 080 | A1 | 12/1999 |
| EP | 1 057 638 | A2 | 12/2000 |
| JP | 10-505920 | A | 6/1998 |
| JP | 11-300951 | A | 11/1999 |
| JP | 2000-501176 | A | 2/2000 |
| JP | 2000-79693 | A | 3/2000 |
| JP | 2000-343706 | A | 12/2000 |
| JP | 2001-296110 | A | 10/2001 |
| JP | 2002-219108 | A | 8/2002 |
| JP | 2003-57599 | A | 2/2003 |
| JP | 2005-164938 | A | 6/2005 |
| JP | 2006-352053 | A | 12/2006 |
| JP | 2011-17652 | A | 1/2011 |
| JP | 2011-185790 | A | 9/2011 |
| JP | 2013-7680 | A | 1/2013 |
| WO | 97/19325 | A1 | 5/1997 |
| WO | 98/10242 | A1 | 3/1998 |
| WO | WO 2013071914 | A1 * | 5/2013 ............. G01B 11/18 |

OTHER PUBLICATIONS

International Search Report dated Jun. 3, 2014 in International Application No. PCT/JP2014/054826.
Written Opinion of the International Searching Authority dated Jun. 3, 2014 in International Application No. PCT/JP2014/054826, 3 pages.
Nobuhira Tanaka, et al., "Simultaneous Measurement of Strain and Temperature Using Birefringence Effect of an FBG Sensor", Ninth Materials and Processing Conference, Nos. 01-26, The Japan Society of Mechanical Engineers, (Nov. 2, 2001), pp. 33-34.
Nobuhira Tanaka et al., "Strain Measurement by the Smart Patch Using FBG Sensors", 43rd Proceedings of the JSASS/JSME Structures Conference, The Japan Society for Aeronautical and Space Sciences, (Aug. 1, 2001), pp. 209-212.
M. Flores de Paco, Extended European Search Report dated Dec. 14, 2016 in corresponding European patent application No. 14797172. 5, pp. 1-9.
Lin Niu, Office Action dated Dec. 29, 2016 in corresponding Chinese patent application No. 201480021967.6 (with English translation), pp. 1-16.
Joji Tsukamoto, Office Action dated Jul. 5, 2016 in Japanese patent application No. 2015-516958 (with English translation), pp. 1-13.
Hiroshi Goto, International Search Report dated Mar. 22, 2016 in International (PCT) Application No. PCT/JP2016/050229, pp. 1-4.
Hiroshi Goto, Written Opinion of the International Searching Authority dated Mar. 22, 2016 in International (PCT) Application No. PCT/JP2016/050229, pp. 1-10.
Takeda et al., "Recent Advances in Cure Process Modeling and Monitoring Methods of Advanced Composite Materials/Structures", Transactions of the Japan Society of Mechanical Engineers Series A, vol. 78, No. 795: pp. 1495-1505 (2012).

* cited by examiner

BONDED STRUCTURE AND BONDING-CONDITION DETECTING METHOD

TECHNICAL FIELD

This invention relates to bonded structures and bonding-condition detecting methods.

BACKGROUND ART

Conventionally, carbon fiber composite materials have been used, for example, in airplane structures that require weight reduction.

As a method of monitoring resin hardening of a carbon fiber composite material, there is a method that uses an optical fiber having a grating sensor provided inside, as described in the Japanese Translation of PCT International Application, Publication NO. 2000-501176.

Generally, members such as carbon fiber composite materials are joined together by using fasteners such as rivets or bolts.

When joining members together, although it is optimal to use an adhesive from the viewpoints of weight reduction, working efficiency, etc., this requires the evaluation of bonding quality. The evaluation of bonding quality is conducted, for example, by way of ultrasonic testing after members are joined together by using an adhesive.

Technical Problem

With ultrasonic testing, however, although it is possible to detect the occurrence of a void in an adhesive layer or a defect such as detachment of a member, it is not possible to evaluate the strength of bonding. This is because the strength of bonding depends on factors such as a pressure applied to members during bonding but it is not possible to inspect the pressure in ultrasonic testing. Furthermore, ultrasonic testing requires time and labor and also requires a certified inspector.

Furthermore, in the case where the members are carbon fiber composite materials, for example, the members are bonded together during autoclave shaping. During autoclave shaping, although the pressure in the autoclave and the pressure in the bag are measured, the pressure at the bonding region itself is not measured.

In consideration of these facts, in the case where members are joined together by bonding, structures are designed with considerable safety margins, or fasteners are used for joining instead of adhesive bonding at regions where safety is emphasized.

SUMMARY OF THE INVENTION

The present invention has been made in view of this situation, and it is an object thereof to provide a bonded structure and a bonding-condition detecting method that make it possible to determine whether members are bonded together appropriately.

Solution to Problem

In order to solve the problem described above, a bonded structure and a bonding-condition detecting method according to the present invention employ the following solutions.

A bonded structure according to a first aspect of the present invention includes a first member, a second member, an adhesive that bonds together the first member and the second member, and an optical fiber sandwiched between the first member and the second member, and the bonding condition between the first member and the second member is detected based on birefringence of the optical fiber.

With this configuration, the first member and the second member are bonded together by using the adhesive. The first member and the second member are bonded together by applying an appropriate pressure with the adhesive sandwiched therebetween. The optical fiber sandwiched between the first member and the second member is used to detect the bonding condition between the first member and the second member based on birefringence.

When a pressure is not applied to the optical fiber, the light spectrum has only one peak. On the other hand, when a pressure is applied to the optical fiber only from a predetermined direction, the sectional shape of the optical fiber, which was originally a circular shape, is deformed to become, for example, an elliptical shape (a flattened circular shape or an elongated circular shape), so that the shape of the light spectrum changes so as to have multiple (e.g., two) peaks. This is birefringence of the optical fiber, and the optical fiber is used as a pressure sensor.

That is, when the first member and the second member are bonded together by appropriately applying a pressure, a pressure is applied to the optical fiber from both directions associated with the first member and the second member. Thus, the light spectrum of the optical fiber exhibits multiple peaks due to birefringence. The bonding condition between the first member and the second member is detected by using the optical fiber as a pressure sensor as described above.

As described above, with this configuration, since the bonding condition between the first member and the second member is detected based on birefringence of the optical fiber, it is possible to determine whether these members are bonded together appropriately.

In the first aspect, preferably, the first member and the second member are laminates of carbon fiber composite materials, and the bonding condition between the first member and the second member is detected based on birefringence of the optical fiber in a case where the first member and the second member are bonded together by using a pressurizing device.

With this configuration, it is possible to determine whether members are bonded together appropriately in a case where the laminates of carbon fiber composite materials are bonded together as members.

In the first aspect, preferably, the first member and the second member sandwiching the adhesive and the optical fiber are covered with a bag, the pressure inside the bag is set to less than the atmospheric pressure, and the bonding condition between the first member and the second member is detected based on birefringence of the optical fiber while a pressure is being applied inside an autoclave.

With this configuration, it is possible to determine more appropriately whether members are bonded together appropriately in a case where the laminates of carbon fiber composite materials are bonded together as members.

In the first aspect, preferably, a solid object is inserted between the optical fiber and at least one of the first member and the second member.

With this configuration, it is possible to determine whether members are bonded together appropriately even when the members have not yet been bonded together or are being bonded together.

In the first aspect, preferably, the solid object is inserted between the optical fiber and the adhesive.

With this configuration, it is possible to determine more accurately whether members are bonded together appropriately even when the members have not yet been bonded together or are being bonded together.

In the first aspect, preferably, the solid object is formed by hardening an adhesive of the same kind as the adhesive.

With this configuration, since the solid object and the adhesive become integrated in the bonding process of the bonded structure, the solid object does not become an impurity in the bonded structure.

A bonding-condition detecting method according to a second aspect of the present invention includes a first step of bonding together a first member and a second member by using an adhesive with an optical fiber sandwiched therebetween and a second step of detecting the bonding condition between the first member and the second member based on birefringence of the optical fiber.

Advantageous Effects of Invention

According to the present invention, a superior advantage is afforded in that it is possible to determine whether members are bonded together appropriately.

DESCRIPTION OF EMBODIMENTS

Now, an embodiment of a bonded structure and a bonding-condition detecting method according to the present invention will be described with reference to the drawings.

[First Embodiment]

Here, a first embodiment of the present invention will be described.

Figure 1:
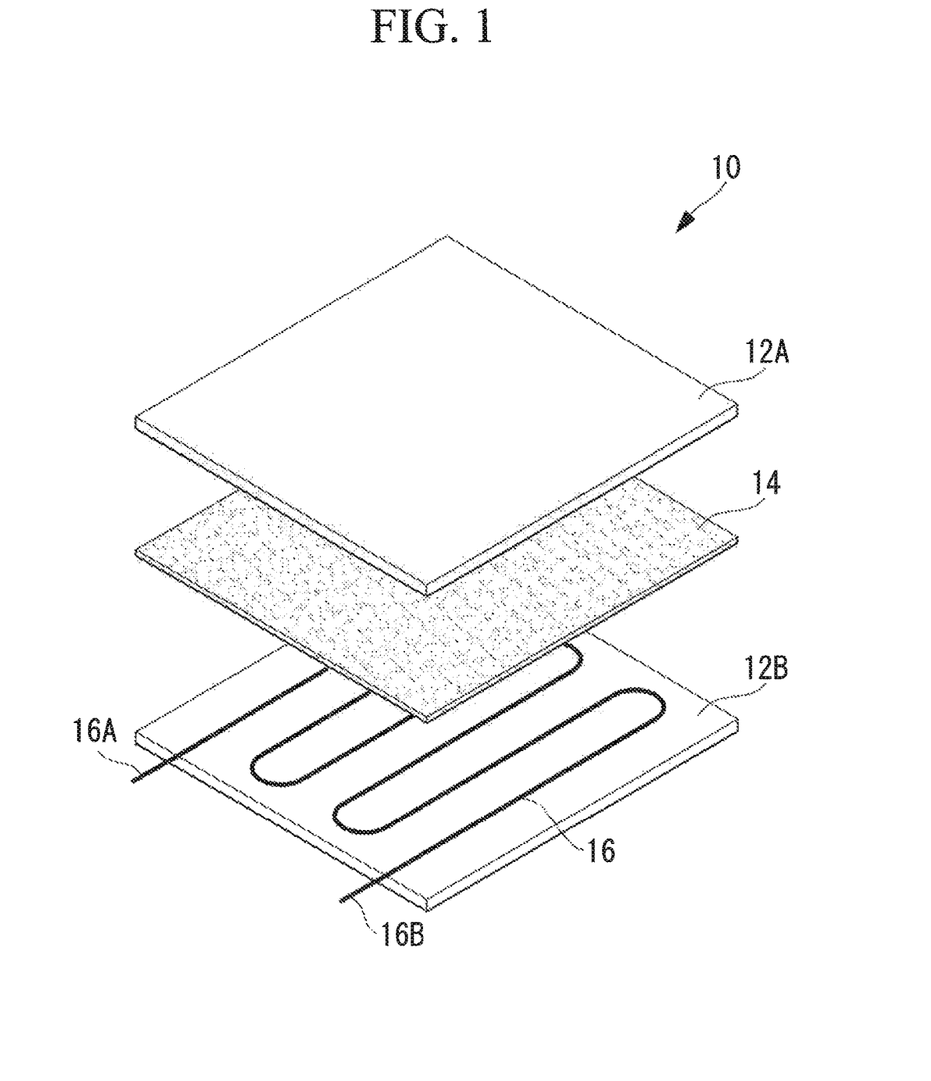
FIG. 1 is an exploded perspective view showing a bonded structure according to a first embodiment of the present invention.

FIG. 1 is an exploded perspective view showing a bonded structure according to the first embodiment. In the first embodiment, as an example, bonded members are laminates of carbon fiber composite materials. Furthermore, for example, multiple bonded structures 10 are combined for use as structural members of airplanes, automobiles, wind turbines, etc.

The bonded structure 10 includes a laminate 12A, a laminate 12B, an adhesive 14 that bonds together the laminate 12A and the laminate 12B, and an optical fiber 16 sandwiched between the laminate 12A and the laminate 12B. The optical fiber 16 is used as a sensor (optical fiber sensor) for detecting the bonding condition between the laminate 12A and the laminate 12B based on birefringence. For example, the optical fiber 16 is a single mode fiber with a cladding diameter of 125 μm and a circular cross section.

The adhesive 14 is formed, for example, as a bonding layer. Although there is no particular limitation as to the kind of the adhesive 14, for example, an epoxy-resin-based adhesive can be used.

Before the laminates 12 A and 12B are bonded together via the adhesive 14, at least one of them is hardened.

Furthermore, although the planar shapes of the laminates 12A and 12B shown in FIG. 1 are rectangular, this is just an example, and the planar shapes of the laminates 12A and 12B are not limited to rectangular shapes. Furthermore, the shapes of the laminates 12A and 12B need not necessarily be planar shapes.

The optical fiber 16 shown in FIG. 1 is bent multiple times, and a light input end 16A and a light output end 16B thereof protrude from the same sides of the laminates 12A and 12B. However, this is just an example. The optical fiber 16 need not necessarily be sandwiched in a bent form, and the input end 16A and output end 16B may protrude from different sides of the laminates 12A and 12B. Furthermore, light may be input to and output from the same end of the optical fiber 16.

Furthermore, although the optical fiber 16 shown in FIG. 1 is sandwiched between the laminate 12A and the laminate 12B so as to be embedded in the adhesive 14, there is no limitation to this form, and the optical fiber 16 need not be embedded in the adhesive 14.

Figure 2:
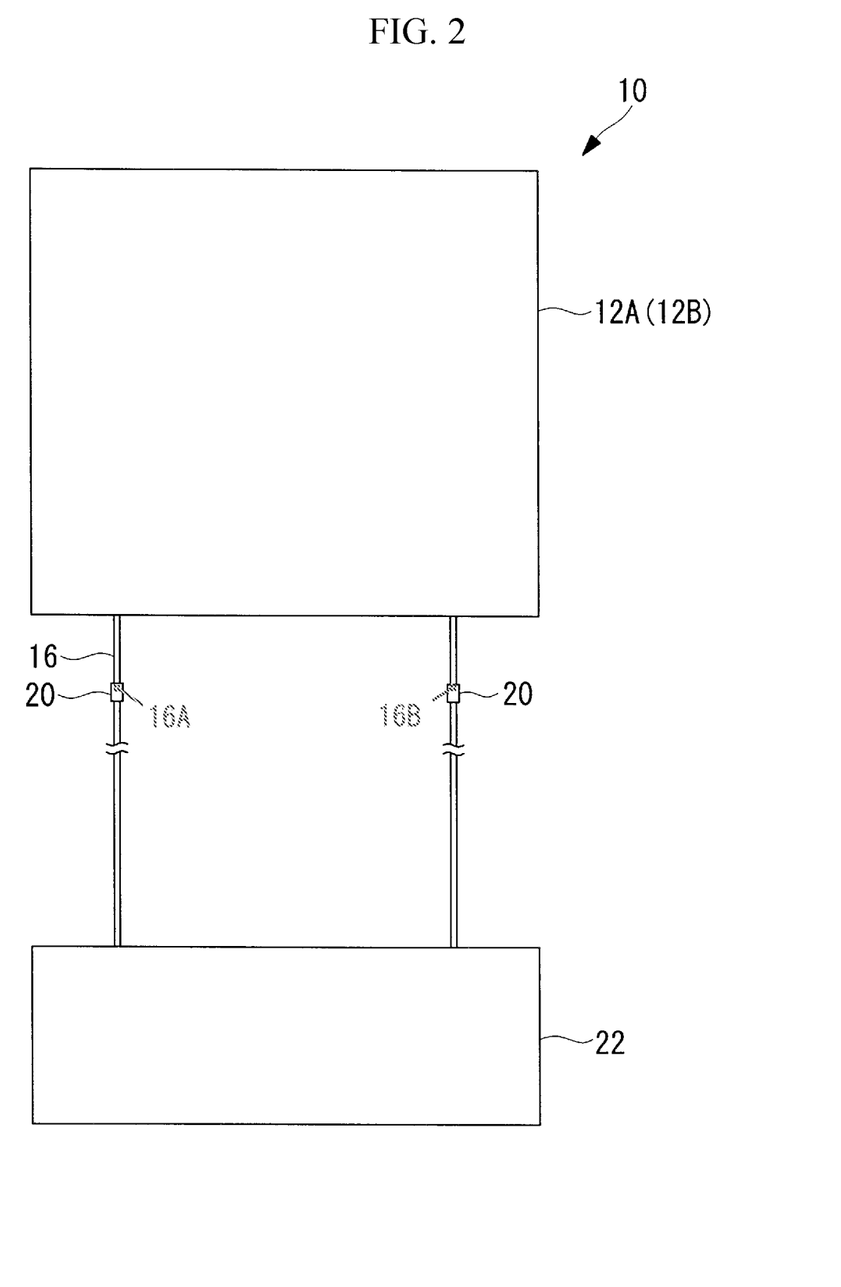
FIG. 2 is a schematic plan view of a measurement and diagnosis unit according to the first embodiment of the present invention.

Furthermore, as shown in FIG. 2, the input ends 16A and the output ends 16B of the optical fiber 16 are individually connected to a measurement and diagnosis unit 22 via connectors 20. The measurement and diagnosis unit 22 receives light having a predetermined wavelength from the input end 16A of the optical fiber 16 and detects light that has been transmitted through the optical fiber 16 at the output end 16B to obtain a light spectrum.

The laminates 12A and 12B are bonded together by applying a pressure to them with the adhesive 14 sandwiched therebetween. When the pressure is applied to the laminates 12A and 12B, a pressure is also applied to the optical fiber 16.

Figure 3:
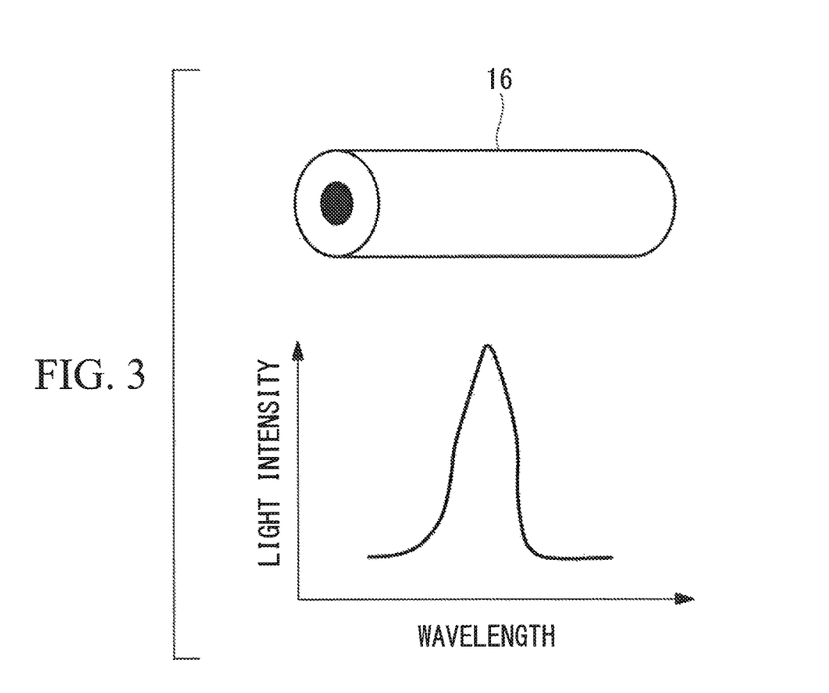
FIG. 3 is a diagram showing the light spectrum in a case where a pressure is not applied to an optical fiber according to the first embodiment of the present invention.
Figure 4:
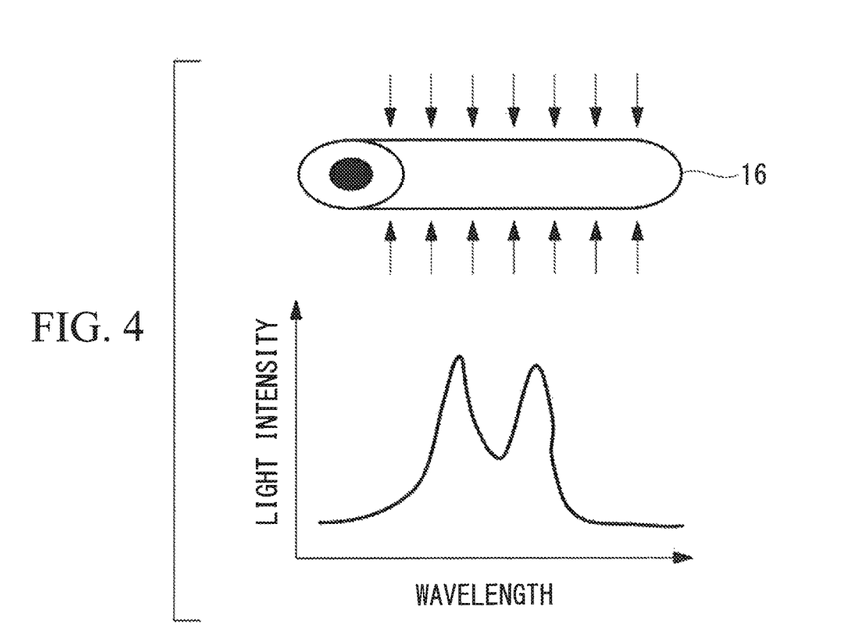
FIG. 4 is a diagram showing the light spectrum in a case where a pressure is applied to the optical fiber according to the first embodiment of the present invention.

When the pressure is not applied to the optical fiber 16, the light spectrum has only one peak, as shown in FIG. 3. On the other hand, when a pressure is applied to the optical fiber 16 only from a predetermined direction, the sectional shape of the optical fiber 16, which was originally a circular shape, is deformed to become, for example, an elliptical shape (a flattened circular shape or an elongated circular shape), as shown in FIG. 4. Thus, the shape of the light spectrum changes so as to have multiple (e.g., two) peaks. This is birefringence of the optical fiber 16.

That is, when the laminates 12A and 12B are bonded together by suitably applying a pressure, a pressure is applied to the optical fiber 16 from both directions associated with the laminate 12A and the laminate 12B, and the light spectrum of the optical fiber 16 exhibits multiple peaks due to birefringence. By using the optical fiber 16 as a pressure sensor as described above, it becomes possible to detect the bonding condition between the laminates 12A and 12B.

In the first embodiment, in which bonded members are the laminates 12A and 12B of carbon fiber composite materials, when the laminates 12A and 12B are bonded together by using a pressurizing device (e.g., an autoclave in the first embodiment), the bonding condition is detected based on birefringence of the optical fiber 16. Thus, in the first embodiment, it is possible to determine whether members are bonded together appropriately when bonding together the laminates 12A and 12B of carbon fiber composite materials as members.

Next, test results for the first embodiment will be described by using FIGS. 5 and 6.

Figure 5:
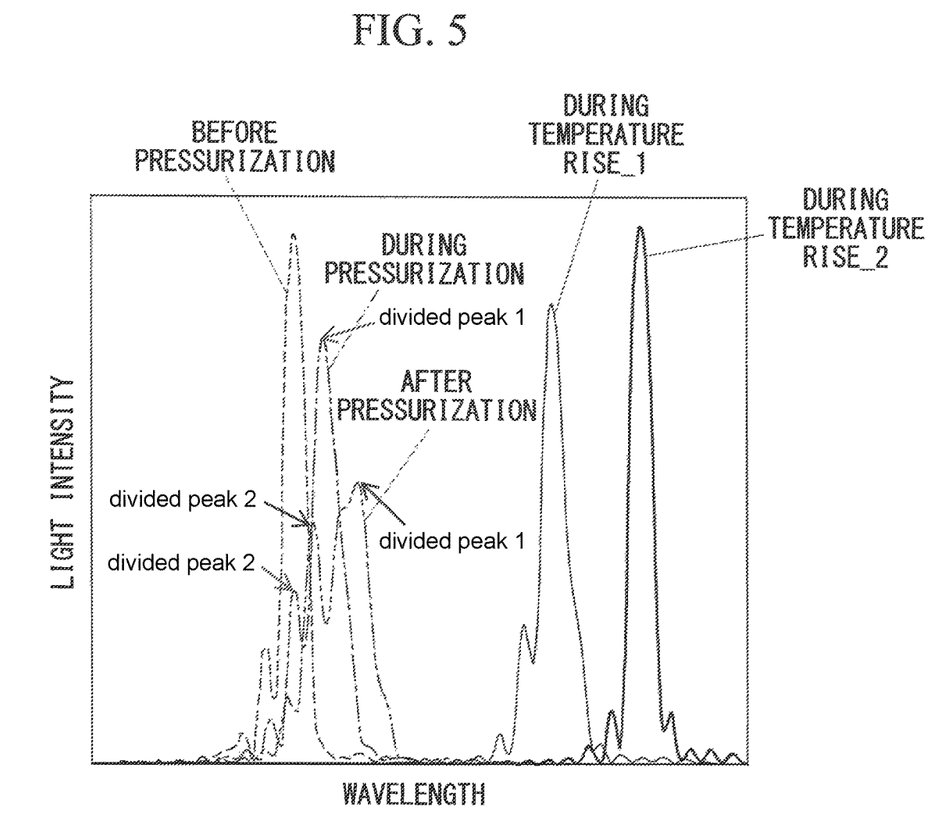
FIG. 5 is a graph showing changes in the shape of the light spectrum of the optical fiber in a process in which the laminates to be bonded according to the first embodiment of the present invention were covered with a bag, the pressure inside the bag was set to less than the atmospheric pressure, and the pressure and temperature inside an autoclave were raised.
Figure 6:
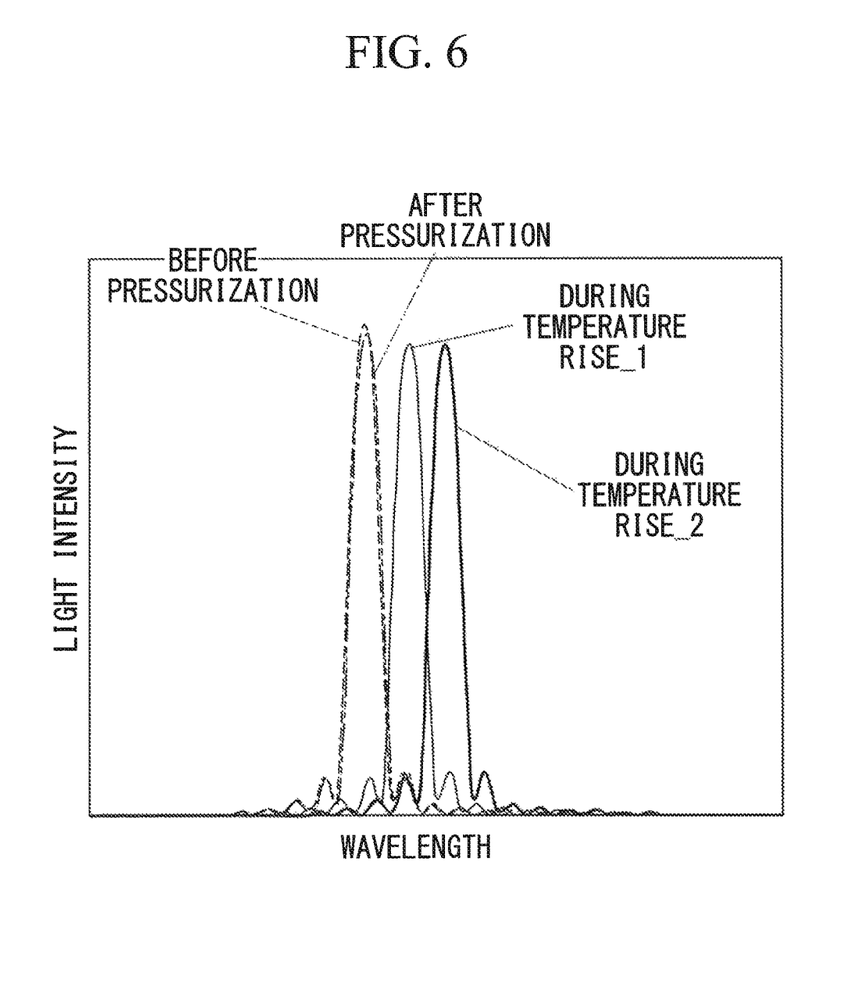
FIG. 6 is a graph showing changes in the shape of the light spectrum of the optical fiber in a process in which the laminates to be bonded according to the first embodiment of the present invention were not covered with a bag, and the pressure and temperature inside an autoclave were raised.

FIGS. 5 and 6 show the results of a test in which unhardened adhesive 14 was sandwiched between the laminates 12A and 12B and the optical fiber 16 was embedded between the adhesive 14 and the laminate 12A and the laminate 12B.

FIG. 5 is a graph showing changes in the light spectrum of the optical fiber 16 in a process in which the laminates 12A and 12B were covered with a bag having an internal pressure less than the atmospheric pressure (vacuum) and the pressure and temperature inside an autoclave were raised.

As shown in FIG. 5, before a pressure was applied inside the autoclave, only one peak appeared in the light spectrum. While a pressure was being applied, the peak in the light spectrum became lower and divided into two, and after the pressure was applied, two apparent peaks appeared in the light spectrum. The two peaks indicate that the sectional shape of the optical fiber 16, which was originally a circular shape, was deformed and changed to an elliptical shape due to the pressure applied to the optical fiber 16, which resulted in birefringence. That is, the peaks indicate that a pressure was applied to the laminates 12A and 12B.

In FIG. 5, the peak position shifts to the higher frequency side in the process before, during, and after pressurization. This is because the temperature of the bonded structure 10 rose due to pressurization.

Then, the temperature was raised in the next step. Referring to FIG. 5, the temperature was higher during temperature rise_2 than during temperature rise_1.

While the temperature was being raised, the peak of the light spectrum converged back to one. This is because the viscosity of the adhesive 14 decreased due to the temperature rise, so that the non-axisymmetric pressure applied to the optical fiber 16 only from a predetermined direction decreased, whereby the deformation of the sectional shape of the optical fiber 16 was alleviated. Even when the pressure applied to the optical fiber 16 decreased, a pressure required for bonding was maintained at the laminates 12A and 12B.

Then, the adhesive 14 was hardened after the temperature rise, whereby the laminates 12A and 12B were bonded together.

On the other hand, FIG. 6 shows changes in the light spectrum of the optical fiber 16 in a process in which the laminates 12A and 12B were not covered with a bag and the pressure and temperature inside the autoclave were raised. That is, a hydrostatic pressure was applied to the laminates 12A and 12B.

As shown in FIG. 6, the shape of the light spectrum did not substantially change and remained the same before and after applying a pressure inside the autoclave, without the peak dividing into two.

Furthermore, even during the temperature rise, the shape of the light spectrum did not change except that the peak position shifted to the higher frequency side.

This indicates that, with the hydrostatic pressure, a sufficient pressure required for bonding was not applied to the laminates 12A and 12B due to the occurrence of voids, etc. in the adhesive 14.

The results shown in FIGS. 5 and 6 demonstrate that it is preferable for the bonding structure 10 according to the first embodiment to cover the laminates 12A and 12B sandwiching the adhesive 14 and the optical fiber 16 with a bag and then to reduce the pressure inside the bag to less than the atmospheric pressure and to detect the bonding condition of the laminates 12A and 12B based on birefringence of the optical fiber 16 while a pressure is being applied inside the autoclave.

In the conventional manufacturing process, the bag is vacuum-pumped and is maintained in that state until shaping is finished or is vacuum-pumped and is opened to the atmosphere when the pressure becomes 1 atm or higher. Furthermore, the autoclave is opened to the atmosphere when the adhesive 14 is hardened, cooling is started, and the temperature becomes 60° C. or lower.

On the other hand, in the test for the first embodiment, shown in FIG. 5, the bag is vacuum-pumped and is then opened to the atmosphere before cooling is started after the adhesive 14 is hardened. Furthermore, the autoclave is opened to the atmosphere before cooling is started after the adhesive 14 is hardened.

Accordingly, a pressure is applied continuously to the laminates 12A and 12B until the adhesive 14 is hardened, so that the laminates 12A and 12B are bonded together more reliably.

Furthermore, it was confirmed that when cooling was started with a certain pressure applied, the sectional shape of the optical fiber 16 again changed to an elliptical shape, which resulted in birefringence. In accordance with this phenomenon, multiple (two) peaks again appeared in the light spectrum. By utilizing this phenomenon, it is possible to combine multiple bonded structures 10, for example, for use as a structural member of an airplane, and to detect the detachment status between the laminates 12A and 12B in real time by measuring the light spectrum even while the airplane is in flight. This is because when the laminates 12A and 12B become detached from each other, the change in the sectional shape of the optical fiber 16 is alleviated, so that the light spectrum exhibits only one peak.

[Second Embodiment]

Now, a second embodiment of the present invention will be described.

Figure 7:
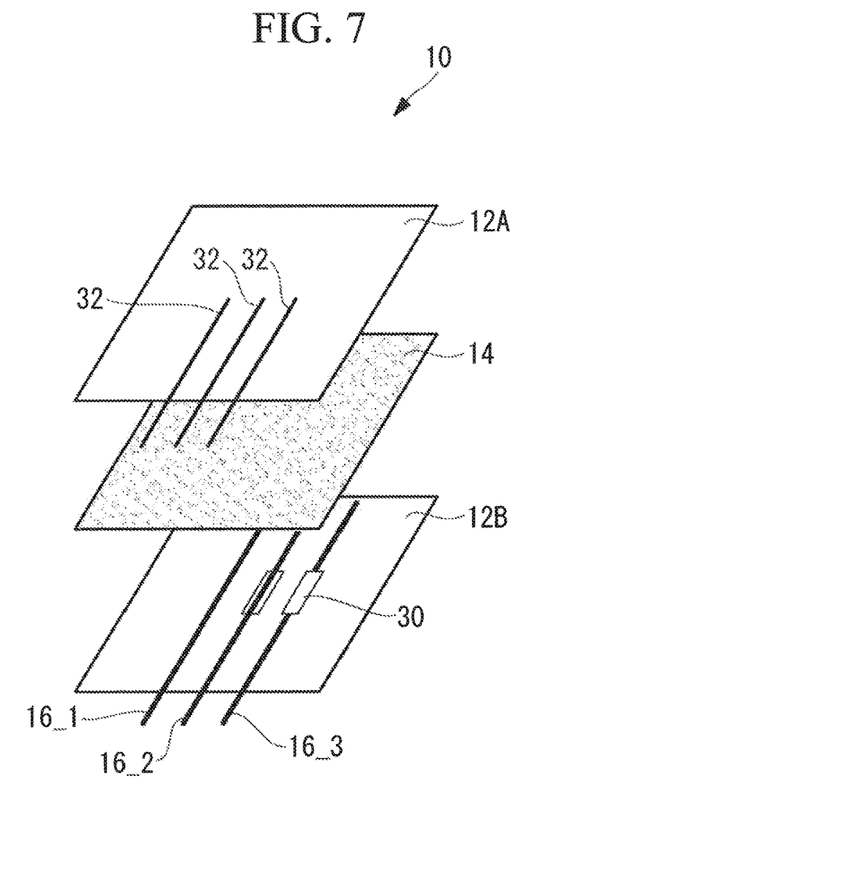
FIG. 7 is an exploded perspective view showing a bonded structure according to a second embodiment of the present invention.
Figure 8:
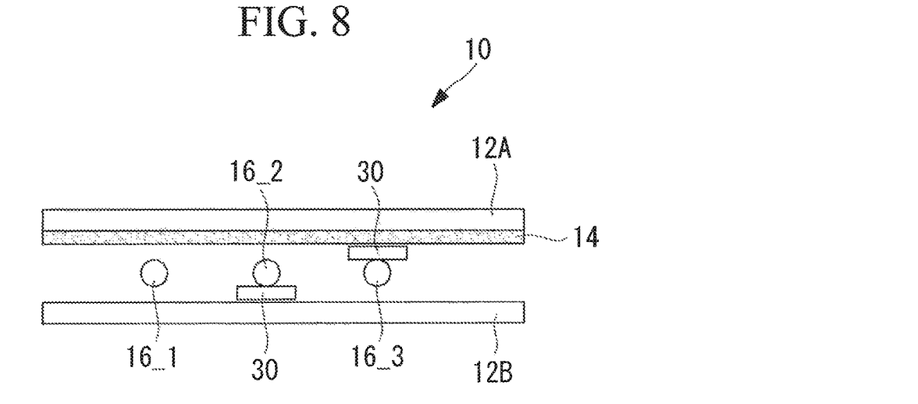
FIG. 8 is an exploded vertical sectional view of the bonded structure according to the second embodiment of the present invention.

FIG. 7 is an exploded perspective view showing a bonded structure 10 according to the second embodiment. FIG. 8 is an exploded vertical sectional view of the bonded structure 10 according to the second embodiment.

As shown in FIGS. 7 and 8, in the bonded structure 10 according to the second embodiment, solid elements 30, which are solid objects, are inserted between the optical fiber 16 and at least one of the laminate 12A and the laminate 12B.

The example shown in FIGS. 7 and 8 is a configuration for the purpose of testing, and in order to measure the difference in changes of the shape of the light spectrum depending on the presence or absence of the solid elements 30, which will be described later, an optical fiber 16_1 with no associated inserted solid element 30 and optical fibers 16_2 and 16_3 with associated inserted solid elements 30 are provided. Furthermore, in order to measure the temperature in the vicinity of each of the optical fibers 16, a temperature sensor 32 is disposed for each of the optical fibers 16 on the top face of the laminate 12A. For example, the temperature sensor 32 is a thermocouple.

A solid element 30 is inserted between the optical fiber 16_2 and the laminate 12B. Furthermore, a solid element 30 is inserted between the optical fiber 16_3 and the adhesive 14.

For example, the solid elements 30 are made of hardened adhesive, and examples thereof include chemical setting, thermosetting, and thermoplastic adhesives.

A chemical setting adhesive is an adhesive whose hardening response progresses, for example, when two liquids, namely, a main agent and a hardening agent, are mixed together. An example thereof is EA9394 from Henkel.

A thermosetting adhesive is an adhesive whose hardening response progresses when heat is applied to the adhesive from outside. An example thereof is FM300-2 from Cytec.

A thermoplastic adhesive is an adhesive whose hardening response progresses when a polymerization reaction occurs due to heat applied to the adhesive and then heat is dissipated. An example thereof is PPS resin (Poly Phenylene Sulfide Resin).

Furthermore, as the solid elements 30, shims such as unhardened prepregs used to adjust the gaps at the bonding regions may be used.

In the second embodiment, as an example of the solid elements 30, an element formed by hardening FM300-2 from Cytec, mentioned above, was used. In the second embodiment, as an example, FM300-2 from Cytec was also used as the adhesive 14.

Since the solid elements 30 are formed by hardening an adhesive of the same kind as the adhesive 14 as described above, so that the solid elements 30 and the adhesive 14 are integrated (assimilated) in the bonding process of the bonded structure 10, the solid elements 30 do not become impurities in the bonded structure 10, and the strength in the vicinity of the regions where the solid elements 30 are inserted is not reduced.

Furthermore, the choice among chemical setting, thermosetting, thermoplastic, and other types of adhesive for use as the solid elements 30 is determined suitably in accordance with the shape of the solid elements 30, the kind of the adhesive 14 used, etc.

Furthermore, for example, the size of the solid elements 30 is a plate shape of 20 mm×5 mm, and their lengthwise direction is aligned with the directions of the optical fibers 16. The solid elements 30 need not be inserted in association with the entire optical fibers 16, and it suffices to insert the solid elements 30 in regions associated with sensing portions of the optical fibers 16. The shape of the solid elements 30 need not be a rectangular shape and may be a square shape, a polygonal shape other than a rectangular shape, a circular shape, etc. Furthermore, the thickness of the solid elements 30 is chosen such that the total thickness of the optical fibers 16 and the solid elements 30 is less than the thickness of the bonding layer formed of the adhesive 14.

Figure 9:
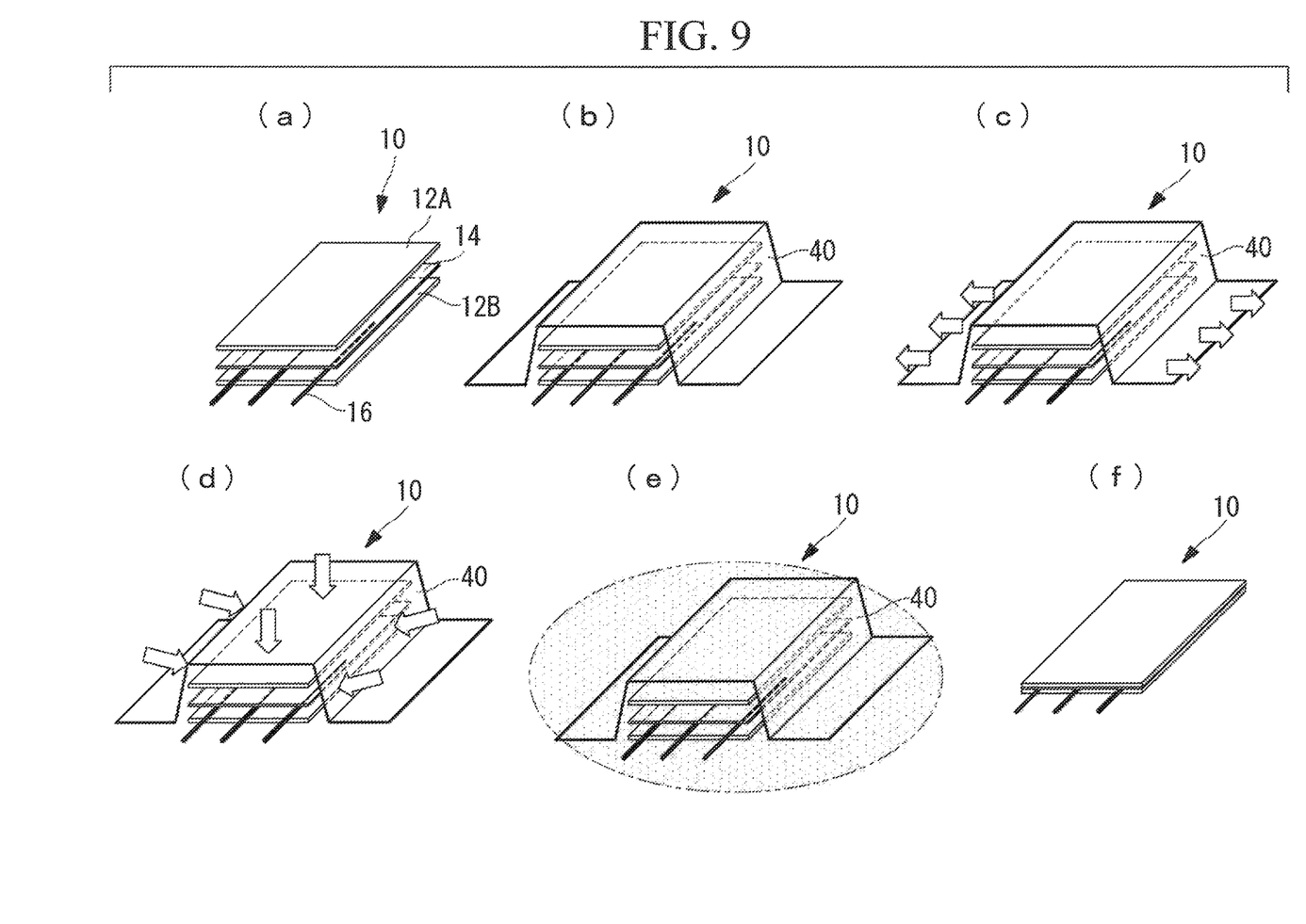
FIG. 9 is a schematic illustration showing a bonding process of the bonded structure according to the second embodiment of the present invention.

FIG. 9 is a schematic illustration showing the bonding process of the bonded structure 10.

First, to form the bonded structure 10, the laminate 12A, the adhesive 14, the optical fibers 16, and the laminate 12B are stacked in that order (FIG. 9(a)).

Then, the laminated assembly is covered with a bag 40 (FIG. 9(b)).

Then, the interior of the bag 40 is vacuum-pumped to set the internal pressure to less than the atmospheric pressure (FIG. 9(c)). This results in a pressure difference of about 1 atm between the interior and exterior of the bag 40.

Then, a predetermined pressure is applied from the outside of the bag 40 (autoclave pressurization) (FIG. 9(d)). This results in a pressure difference exceeding about 1 atm between the interior and exterior of the bag 40.

Then, heat is applied at a predetermined temperature from the outside of the bag 40 (autoclave heating) (FIG. 9(e)). The dotted area shown in FIG. 9(e) exemplifies an area in which hat is applied from the outside.

Then, after cooling for a predetermined period, the hardening of the adhesive 14 is finished, whereby the bonded structure 10 is formed (FIG. 9(f)).

Figure 10:
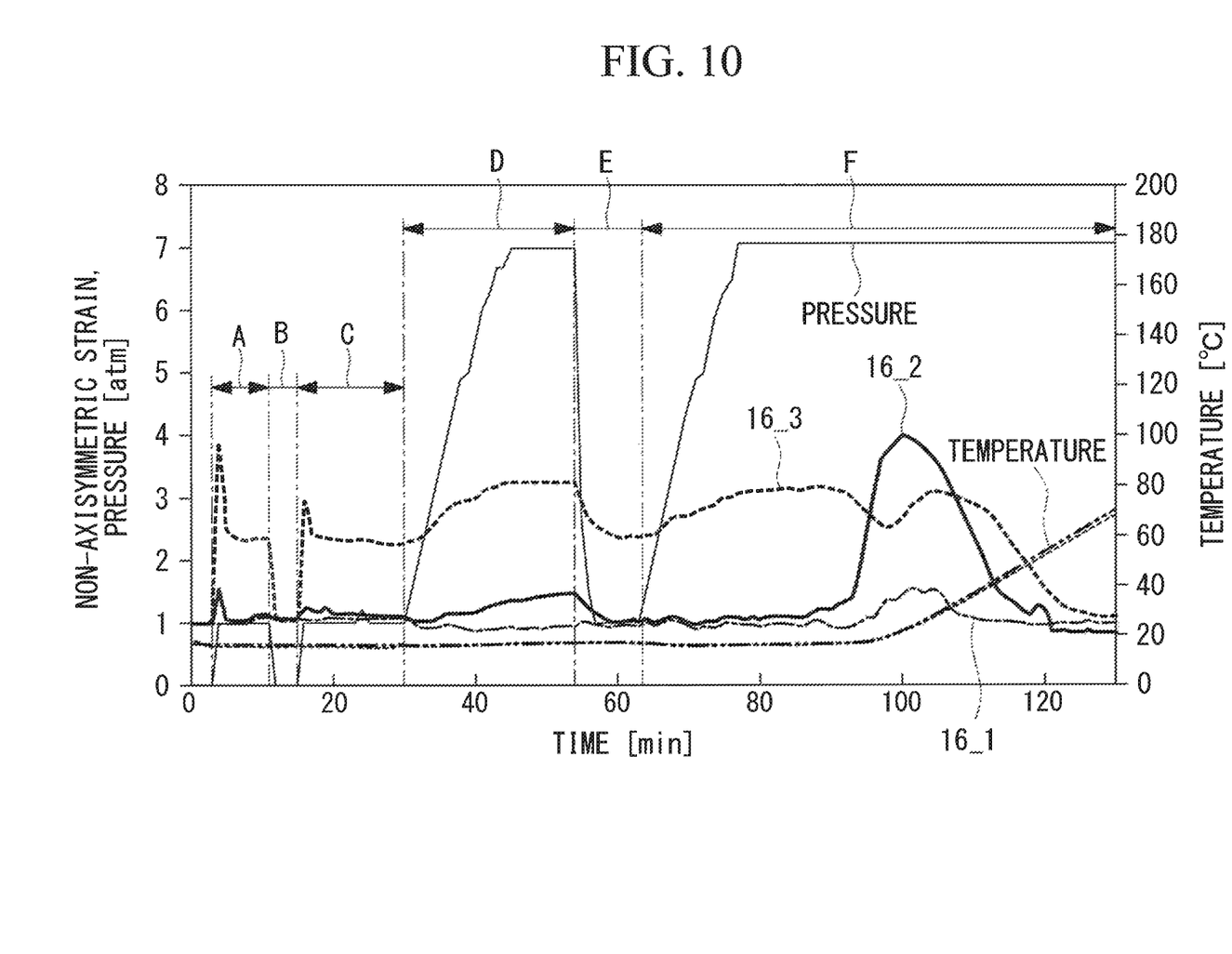
FIG. 10 is a graph showing changes in the amounts of non-axisymmetric strains of optical fibers in an initial pressurizing process according to the second embodiment of the present invention.

FIG. 10 is a graph showing changes in the amounts of non-axisymmetric strains of the optical fibers 16_1, 16_2, and 16_3 in the initial pressurizing process. The initial pressurizing process refers to the process shown in FIGS. 9(c) and (d). The amounts of non-axisymmetric strains refer to the amounts of strains into elliptical shapes caused by pressurization of the optical fibers 16, obtained based on the shape of the light spectrum.

In FIG. 10, the vertical axis represents the pressure difference between the interior and exterior of the bag 40, the temperature, and the amount of non-axisymmetric strain, and the horizontal axis represents time. 0 atm along the vertical axis corresponds to the case where the pressure inside the bag 40 was the atmospheric pressure and a pressure was not applied from the outside.

Furthermore, there were no significant differences among the temperatures measured by the temperature sensors 30 associated with the optical fibers 16_1, 16_2, and 16_3, and the temperatures changed substantially the same over time.

Region A in FIG. 10 corresponds to the case where the interior of the bag 40 was vacuum-pumped (FIG. 9(c)), and the amounts of non-axisymmetric strains of the optical fibers 16_2 and 16_3 increased when the pressure was changed to 1 atm. In the amounts of non-axisymmetric strains in region A, a peak occurred in the initial stage. The reason is as follows. When a pressure was applied to the optical fibers 16_2 and 16_3, although the amounts of non-axisymmetric strains become maximum in the initial stage, since the optical fibers 16_2 and 16_3 entered the solid elements 30 due to the pressure, the stress applied to the optical fibers 16_2 and 16_3 was alleviated, whereby the amounts of non-axisymmetric strains decreased.

Region B corresponds to the case where the vacuum interior of the bag 40 was opened, whereby the non-axisymmetric strains of the optical fibers 16_2 and 16_3 were eliminated. Region B was provided experimentally in order to measure the non-axisymmetric strains of the optical fibers 16_2 and 16_3, and the above operation is not performed in the actual initial pressurizing process.

Region C corresponds to the case where the vacuum pumping of the interior of the bag 40 was resumed, in which the amounts of non-axisymmetric strains of the optical fibers 16_2 and 16_3 increased, similarly to region A.

For both regions A and C, the sensitivity of the optical fiber 16_3, in association with which the solid element 30 was inserted in the gap with the adhesive 14, was higher than the sensitivity of the optical fiber 16_2, in association with which the solid element 30 was inserted in the gap with the laminate 12B.

Therefore, it is preferred to insert the solid elements 30 between the optical fibers 16 and the adhesive 14. This makes it possible to determine more accurately whether members are bonded together appropriately even during the bonding process of the bonded structure 10 in which the laminates 12A and 12B have not yet been bonded together or are being bonded together.

Region D corresponds to the case where autoclave pressurization was performed (FIG. 9(d)), with a maximum pressure of 7 atm. The amounts of non-axisymmetric strains of the optical fibers 16_2 and 16_3 increased as the pressure was applied. The response of the optical fiber 16_2 was slower than the response of the optical fiber 16_3.

Region E corresponds to the case where the pressure was removed, at which time the pressure decreased to 1 atm and the non-axisymmetric strains of the optical fibers 16_2 and 16_3 were eliminated. Region E was provided experimentally in order to measure the non-axisymmetric strains of the optical fibers 16_2 and 16_3, and the above operation is not performed in the actual initial pressurizing process.

Region F corresponds to the case where the autoclave pressurization was resumed, at which time the amounts of non-axisymmetric strains of the optical fibers 16_2 and 16_3 increased, similarly to region D.

The amounts of non-axisymmetric strains of the optical fibers 16_2 and 16_3 increased as the pressure was applied. However, when heating was started, the adhesive 14 gradually softened, so that the stress applied to the optical fibers 16_2 and 16_3 was alleviated, whereby the amounts of non-axisymmetric strains gradually decreased.

Changes in the amount of non-axisymmetric strain of the optical fiber 16_1, in association with which no solid element 30 was inserted, were smaller compared with those of the optical fibers 16_2 and 16_3.

The reason is that, since no solid element 30 was inserted in association with the optical fiber 16_1, when a pressure was applied, the optical fiber 16_1 entered the adhesive 14 instead of a stress being applied thereto, so that the shape of the optical fiber 16_1 did not change. On the other hand, the optical fibers 16_2 and 16_3, in association with which the solid elements 30 were inserted, were hindered from entering the adhesive 14 by the solid elements 30. Thus, a stress was applied to the optical fibers 16_2 and 16_3, and the shapes thereof changed, which resulted in changes in the amounts of non-axisymmetric strains. This made it possible to determine whether members are bonded together appropriately even during the bonding process of the bonded structure 10.

Furthermore, the test results shown in FIG. 10 demonstrate that the sensitivity of the optical fiber 16_3, in association with which the solid element 30 was inserted in the gap with the adhesive 14, was higher than the sensitivity of the optical fiber 16_2, in association with which the solid element 30 was inserted in the gap with the laminate 12B. This is because the solid element 30 inserted in the gap with the adhesive 14 more strongly hinders the associated optical fiber 16 from entering the adhesive 14 compared with the case where the solid element 30 was inserted in the gap with the laminate 12B.

Therefore, it is preferred to insert the solid elements 30 between the optical fibers 16 and the adhesive 14. Accordingly, in the second embodiment, it is possible to more accurately determine whether members are bonded together appropriately even during the bonding process of the bonded structure 10 in which the laminates 12A and 12B have not yet been bonded together or are being bonded together.

Figure 11:
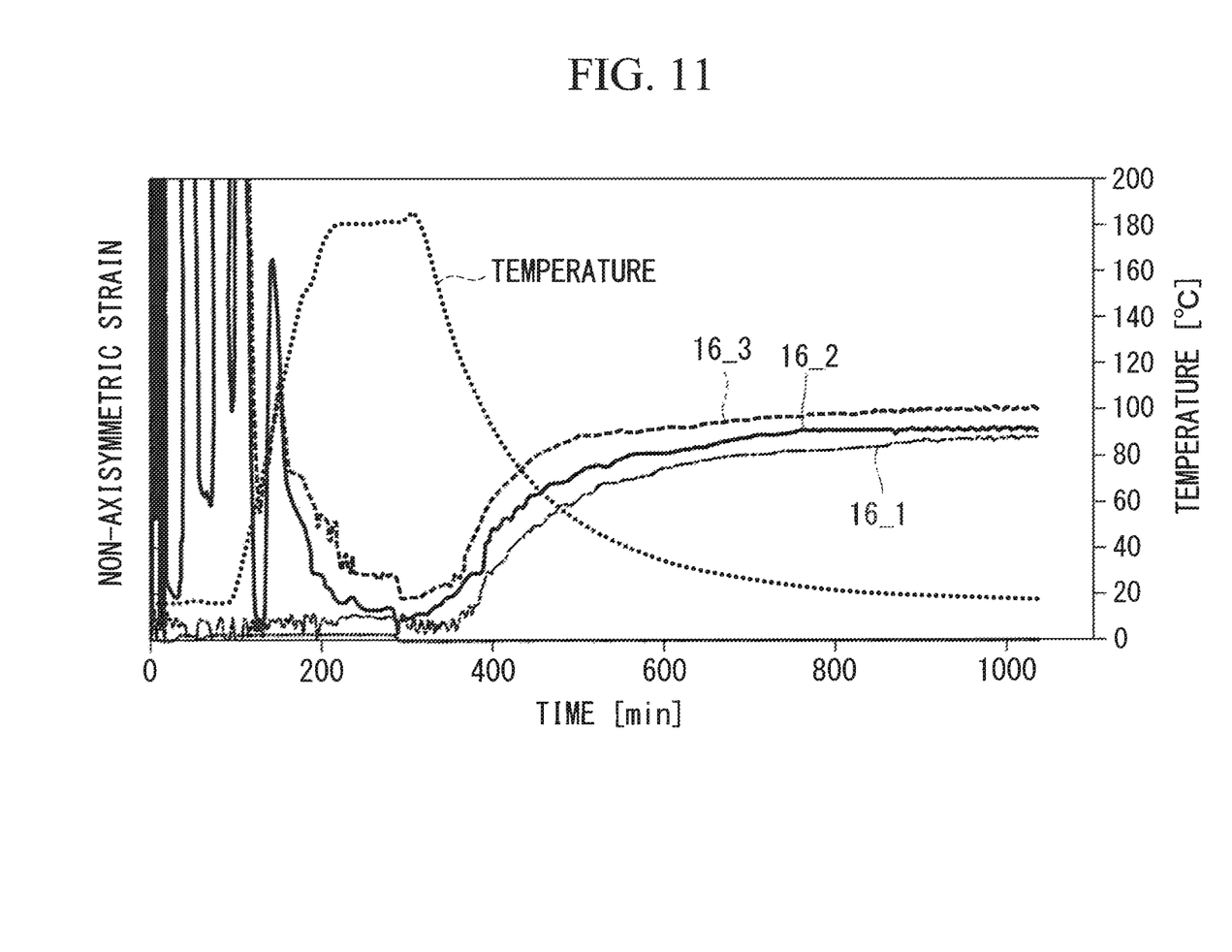
FIG. 11 is a graph showing changes in the amounts of non-axisymmetric strains of optical fibers in a heating and cooling process according to the second embodiment of the present invention.

FIG. 11 is a graph showing changes in the amounts of non-axisymmetric strains of the optical fibers 16_1, 16_2, and 16_3 in a heating and cooling process. The initial pressurizing process is shown in FIGS. 9 (e) and (f).

In FIG. 11, the vertical axis represents the amount of non-axisymmetric strain and the temperature, and the horizontal axis represents time.

It is to be noted that although the amounts of non-axisymmetric strains of the optical fibers 16_2 and 16_3 increased and decreased even before heating was started (from 0 to just after 100 minutes), the increases and decreases were attributable to large variations in the light spectrum due to vacuum pumping, pressurizing, etc. of the bag 40, which resulted in incorrect calculation of the non-axisymmetric strains.

As shown in FIG. 11, in the early stage of heating, the amounts of non-axisymmetric strains of the optical fibers 16_2 and 16_3 were large. On the other hand, there was no significant change in the amount of non-axisymmetric strain of the optical fiber 16_1.

The reason for this is as follows. Since the adhesive 14 softened when heated, the optical fiber 16_1 entered the adhesive 14 instead of a stress being applied thereto. On the other hand, the optical fibers 16_2 and 16_3 were hindered from entering the adhesive 14 by the solid elements 30, so that a stress was applied to the optical fibers 16_2 and 16_3, whereby the shapes thereof changed.

However, the adhesive 14 further softened as the temperature rose, and the stress applied to the optical fibers 16_2 and 16_3 was alleviated, so that the amounts of non-axisymmetric strains gradually decreased.

As for the optical fiber 16_1, in association with which no solid element 30 was inserted, there was no significant change in the amount of non-axisymmetric strain even when the temperature rose.

When heating was finished, the temperature fell, and cooling was started, the adhesive 14 hardened, and the stress applied to the optical fibers 16_1, 16_2, and 16_3 increased. Accordingly, the amounts of non-axisymmetric strains of the optical fibers 16_1, 16_2, and 16_3 increased.

Figure 12:
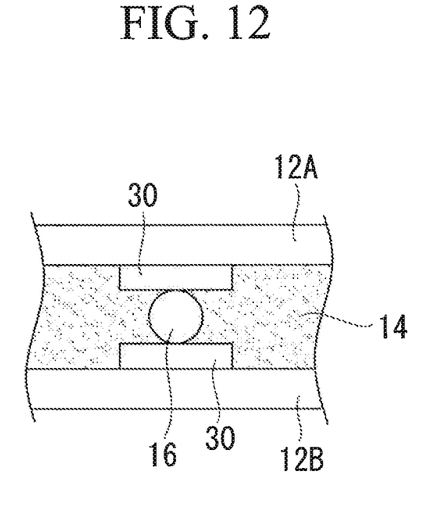
FIG. 12 is a vertical sectional view of the bonded structure according to the second embodiment of the present invention.

FIG. 12 is a vertical sectional view showing an example in which solid elements 30 are inserted between the optical fiber 16 and the laminate 12A and the optical fiber 16 and the laminate 12B. In the case of this mode, it is necessary to insert the solid elements 30 such that the optical fiber 16 becomes embedded in the adhesive 14 after the bonded structure 10 is hardened.

Figure 13:
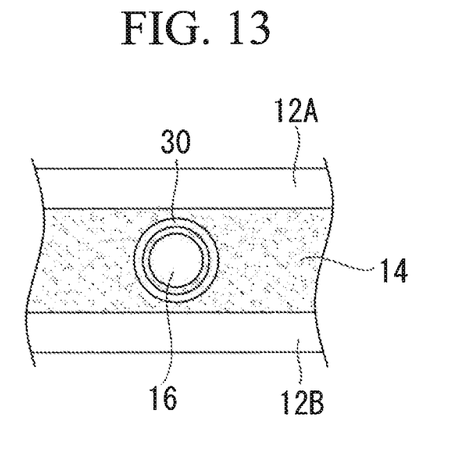
FIG. 13 is a vertical sectional view of the bonded structure according to the second embodiment of the present invention.
Figure 14:
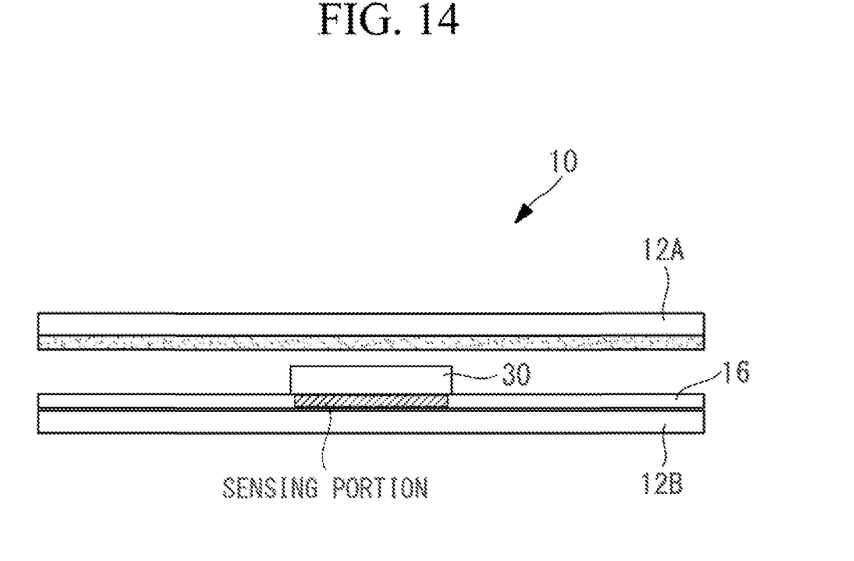
FIG. 14 is a vertical sectional view of the bonded structure according to the second embodiment of the present invention.

FIG. 13 is a vertical sectional view showing an example where the solid element 30 has a tube shape instead of a plate shape. Also in the case of this mode, it is necessary to insert the solid element 30 such that the optical fiber 16 becomes embedded in the adhesive 14 after the bonded structure 10 is hardened.

As described hereinabove, in the bonded structure 10 according to the second embodiment, the solid element 30 is inserted between the optical fiber 16 and at least one of the laminate 12A and the laminate 12B.

Accordingly, with the bonded structure 10 according to the second embodiment, it is possible to determine whether members are bonded together appropriately even when the laminates 12A and 12B have not yet been bonded together or are being bonded together.

Although the present invention has been described in the context of the above-described embodiments, the technical scope of the present invention is not limited to the scopes of the above-described embodiments. It is possible to make various modifications and improvements to the above-described embodiments without departing from the scope of the invention, and the modes involving such modifications and improvements are also included in the technical scope of the present invention.

For example, although the above embodiments have been described in the context of examples where the bonded members are the laminates 12A and 12B of carbon fiber composite materials, without limitation thereto, according to the present invention, for example, the bonded members may be fiber-reinforced resin-based composite materials reinforced with glass fibers, etc. or metallic materials such as aluminum alloys.

{Reference Signs List}

| | |
|---|---|
| 10 | Bonded structure |
| 12A | Laminate |
| 12B | Laminate |
| 14 | Adhesive |
| 16 | Optical fiber |
| 30 | Solid element |

The invention claimed is:

1. A bonded structure comprising:
a first member;
a second member;
a first adhesive that bonds the first member and the second member together; and
an optical fiber sandwiched between the first member and the second member,
wherein a solid object is inserted between the optical fiber and at least one of the first member and the second member, the solid object being formed by hardening a second adhesive,
wherein the solid object has a length covering only sensing portions of the optical fiber,
wherein at least one of the first member and the second member is hardened before the first member and the second member are bonded together via the first adhesive, and
wherein a bonding condition between the first member and the second member is detected based on birefringence of the optical fiber.

2. The bonded structure according to claim 1,
wherein the first member and the second member are laminates of carbon fiber composite materials, and
wherein the bonding condition between the first member and the second member is detected based on birefringence of the optical fiber in a case where the first member and the second member are bonded together using a pressurizing device.

3. The bonded structure according to claim 2, wherein the first member and the second member sandwiching the first adhesive and the optical fiber are covered with a bag, a pressure inside the bag is set to less than atmospheric pressure, and the bonding condition between the first member and the second member is detected based on birefringence of the optical fiber while a pressure is being applied inside an autoclave.

4. The bonded structure according to claim 1, wherein the solid object is inserted between the optical fiber and the first adhesive.

5. The bonded structure according to claim 1, wherein the optical fiber is bent multiple times.

6. The bonded structure according to claim 1, wherein a light input end of the optical fiber and a light output end of the optical fiber protrude from a same side of the first member or the second member.

7. The bonded structure according to claim 1, wherein a thickness of the solid object is defined such that a total thickness of the optical fiber and the solid object is less than a thickness of a bonding layer formed of the first adhesive.

8. A bonding-condition detecting method comprising:
bonding a first member and a second member together using a first adhesive with an optical fiber sandwiched therebetween; and
detecting a bonding condition between the first member and the second member based on birefringence of the optical fiber,
wherein a solid object is inserted between the optical fiber and at least one of the first member and the second member, the solid object being formed by hardening a second adhesive,
wherein the solid object has a length covering only sensing portions of the optical fiber, and
wherein at least one of the first member and the second member is hardened before the first member and the second member are bonded together via the first adhesive.

9. The bonding-condition detecting method according to claim 8, wherein the optical fiber is bent multiple times.

10. The bonding-condition detecting method according to claim 8, wherein a light input end of the optical fiber and a light output end of the optical fiber protrude from a same side of the first member or the second member.

* * * * *